US011819285B2

(12) United States Patent
Jasperson et al.

(10) Patent No.: US 11,819,285 B2
(45) Date of Patent: Nov. 21, 2023

(54) MAGNETIC INTERFERENCE DETECTION SYSTEMS AND METHODS

(71) Applicant: COVIDIEN LP, Mansfield, MA (US)

(72) Inventors: Keith E. Jasperson, Andover, MN (US); Michael R. Weisenberger, Minneapolis, MN (US); H. Aaron Christmann, White Bear Lake, MN (US)

(73) Assignee: Covidien LP, Mansfield, MA (US)

( * ) Notice: Subject to any disclaimer, the term of this patent is extended or adjusted under 35 U.S.C. 154(b) by 1168 days.

(21) Appl. No.: 16/376,106

(22) Filed: Apr. 5, 2019

(65) Prior Publication Data

US 2020/0315712 A1 Oct. 8, 2020

(51) Int. Cl.
*A61B 34/20* (2016.01)
*A61B 17/00* (2006.01)

(52) U.S. Cl.
CPC .............. *A61B 34/20* (2016.02); *A61B 17/00* (2013.01); *A61B 2017/00119* (2013.01); *A61B 2017/00199* (2013.01); *A61B 2034/2051* (2016.02); *A61B 2562/0223* (2013.01)

(58) Field of Classification Search
CPC .............. A61B 34/20; A61B 17/00; A61B 2017/00119; A61B 2017/00199; A61B 2034/2051; A61B 2562/0223; A61B 5/062; G01R 33/0206; G01R 33/028; G01R 33/007; G01R 31/001
See application file for complete search history.

(56) References Cited

U.S. PATENT DOCUMENTS

| | | | |
|---|---|---|---|
| 5,629,622 A | 5/1997 | Scampini | |
| 5,647,379 A | 7/1997 | Meltzer | |
| 5,694,952 A | 12/1997 | Lidman et al. | |
| 6,082,366 A * | 7/2000 | Andra | A61B 5/073 128/899 |
| 6,493,573 B1 * | 12/2002 | Martinelli | A61B 34/20 324/257 |
| 6,937,906 B2 | 8/2005 | Terry et al. | |

(Continued)

FOREIGN PATENT DOCUMENTS

| | | |
|---|---|---|
| BR | 0013237 A | 7/2003 |
| BR | 0116004 A | 6/2004 |
| CZ | 486540 | 9/2016 |
| CZ | 2709512 | 8/2017 |

(Continued)

OTHER PUBLICATIONS

Extended European Search Report dated Sep. 24, 2020, 9 pages.
Communication pursuant to Article 94(3) EPC issued in European Patent Application No. 20167909.9 dated Nov. 2, 2022.

*Primary Examiner* — Sanjay Cattungal
(74) *Attorney, Agent, or Firm* — Weber Rosselli & Cannon LLP (57) ABSTRACT

Electromagnetic navigation systems and methods detect ambient or extraneous magnetic interference by inhibiting the navigation system from generating an electromagnetic field and measuring, with a sensor, the strength of a magnetic field at one or more frequencies of and at one or more phases associated with the electromagnetic field generated by the navigation system. The systems and methods may further determine whether the strength of the magnetic field is greater than a threshold. Based on this determination, an alert or message may be generated.

20 Claims, 4 Drawing Sheets

(56) References Cited

U.S. PATENT DOCUMENTS

| | | | |
|---|---|---|---|
| 7,076,283 B2 | 7/2006 | Cho et al. | |
| 7,688,064 B2 | 3/2010 | Shalgi et al. | |
| 8,335,359 B2 | 12/2012 | Fidrich et al. | |
| 8,600,480 B2 | 12/2013 | Kariv | |
| 8,706,184 B2 | 4/2014 | Mohr et al. | |
| 8,827,934 B2 | 9/2014 | Chopra et al. | |
| 8,994,376 B2 | 3/2015 | Billeres et al. | |
| 9,918,659 B2 | 3/2018 | Chopra et al. | |
| 10,373,719 B2 | 8/2019 | Soper et al. | |
| 10,376,178 B2 | 8/2019 | Chopra | |
| 10,405,753 B2 | 9/2019 | Sorger | |
| 10,478,162 B2 | 11/2019 | Barbagli et al. | |
| 10,480,926 B2 | 11/2019 | Froggatt et al. | |
| 10,524,866 B2 | 1/2020 | Srinivasan et al. | |
| 10,555,788 B2 | 2/2020 | Panescu et al. | |
| 10,610,306 B2 | 4/2020 | Chopra | |
| 10,638,953 B2 | 5/2020 | Duindam et al. | |
| 10,674,970 B2 | 6/2020 | Averbuch et al. | |
| 10,682,070 B2 | 6/2020 | Duindam | |
| 10,706,543 B2 | 7/2020 | Donhowe et al. | |
| 10,709,506 B2 | 7/2020 | Coste-Maniere et al. | |
| 10,772,485 B2 | 9/2020 | Schlesinger et al. | |
| 10,796,432 B2 | 10/2020 | Mintz et al. | |
| 10,823,627 B2 | 11/2020 | Sanborn et al. | |
| 10,827,913 B2 | 11/2020 | Ummalaneni et al. | |
| 10,835,153 B2 | 11/2020 | Rafii-Tari et al. | |
| 10,885,630 B2 | 1/2021 | Li et al. | |
| 2001/0026222 A1* | 10/2001 | Canady, Jr. | A61B 5/113 340/572.1 |
| 2003/0013972 A1 | 1/2003 | Makin | |
| 2007/0078334 A1 | 4/2007 | Scully et al. | |
| 2007/0167743 A1* | 7/2007 | Honda | A61B 5/6831 600/424 |
| 2008/0312530 A1 | 12/2008 | Malackowski et al. | |
| 2008/0319312 A1* | 12/2008 | Eichler | A61B 5/06 600/424 |
| 2009/0284255 A1 | 11/2009 | Zur | |
| 2010/0331671 A1 | 12/2010 | Martinelli et al. | |
| 2011/0156700 A1* | 6/2011 | Kariv | A61B 5/062 324/244 |
| 2011/0160791 A1 | 6/2011 | Ellingson et al. | |
| 2011/0244599 A1* | 10/2011 | Whig | H01L 43/08 257/E21.585 |
| 2012/0165660 A1 | 6/2012 | Wu | |
| 2013/0225972 A1 | 8/2013 | Banville et al. | |
| 2013/0303945 A1 | 11/2013 | Blumenkranz et al. | |
| 2014/0035798 A1 | 2/2014 | Kawada et al. | |
| 2015/0148690 A1 | 5/2015 | Chopra et al. | |
| 2015/0265368 A1 | 9/2015 | Chopra et al. | |
| 2016/0157939 A1 | 6/2016 | Larkin et al. | |
| 2016/0183841 A1 | 6/2016 | Duindam et al. | |
| 2016/0192860 A1 | 7/2016 | Allenby et al. | |
| 2016/0203608 A1* | 7/2016 | Izmirli | A61B 5/1036 382/128 |
| 2016/0287344 A1 | 10/2016 | Donhowe et al. | |
| 2017/0112576 A1 | 4/2017 | Coste-Maniere et al. | |
| 2017/0209071 A1 | 7/2017 | Zhao et al. | |
| 2017/0209072 A1 | 7/2017 | Oren et al. | |
| 2017/0265952 A1 | 9/2017 | Donhowe et al. | |
| 2017/0311844 A1 | 11/2017 | Zhao et al. | |
| 2017/0319165 A1 | 11/2017 | Averbuch | |
| 2018/0078318 A1 | 3/2018 | Barbagli et al. | |
| 2018/0153621 A1 | 6/2018 | Duindam et al. | |
| 2018/0235709 A1 | 8/2018 | Donhowe et al. | |
| 2018/0240237 A1 | 8/2018 | Donhowe et al. | |
| 2018/0256262 A1 | 9/2018 | Duindam et al. | |
| 2018/0263706 A1 | 9/2018 | Averbuch | |
| 2018/0279852 A1 | 10/2018 | Rafii-Tari et al. | |
| 2018/0325419 A1 | 11/2018 | Zhao et al. | |
| 2019/0000559 A1 | 1/2019 | Berman et al. | |
| 2019/0000560 A1 | 1/2019 | Berman et al. | |
| 2019/0008413 A1 | 1/2019 | Duindam et al. | |
| 2019/0038365 A1 | 2/2019 | Soper et al. | |
| 2019/0065209 A1 | 2/2019 | Mishra et al. | |
| 2019/0110839 A1 | 4/2019 | Rafii-Tari et al. | |
| 2019/0175062 A1 | 6/2019 | Rafii-Tari et al. | |
| 2019/0183318 A1 | 6/2019 | Froggatt et al. | |
| 2019/0183585 A1 | 6/2019 | Rafii-Tari et al. | |
| 2019/0183587 A1 | 6/2019 | Rafii-Tari et al. | |
| 2019/0192234 A1 | 6/2019 | Gadda et al. | |
| 2019/0209016 A1 | 7/2019 | Herzlinger et al. | |
| 2019/0209043 A1 | 7/2019 | Zhao et al. | |
| 2019/0216548 A1 | 7/2019 | Ummalaneni | |
| 2019/0239723 A1 | 8/2019 | Duindam et al. | |
| 2019/0239831 A1 | 8/2019 | Chopra | |
| 2019/0250050 A1 | 8/2019 | Sanborn et al. | |
| 2019/0254649 A1 | 8/2019 | Walters et al. | |
| 2019/0269470 A1 | 9/2019 | Barbagli et al. | |
| 2019/0272634 A1 | 9/2019 | Li et al. | |
| 2019/0298160 A1 | 10/2019 | Ummalaneni et al. | |
| 2019/0298451 A1 | 10/2019 | Wong et al. | |
| 2019/0320878 A1 | 10/2019 | Duindam et al. | |
| 2019/0320937 A1 | 10/2019 | Duindam et al. | |
| 2019/0336238 A1 | 11/2019 | Yu et al. | |
| 2019/0343424 A1 | 11/2019 | Blumenkranz et al. | |
| 2019/0350659 A1 | 11/2019 | Wang et al. | |
| 2019/0365199 A1 | 12/2019 | Zhao et al. | |
| 2019/0365479 A1 | 12/2019 | Rafii-Tari | |
| 2019/0365486 A1 | 12/2019 | Srinivasan et al. | |
| 2019/0380787 A1 | 12/2019 | Ye et al. | |
| 2020/0000319 A1 | 1/2020 | Saadat et al. | |
| 2020/0000526 A1 | 1/2020 | Zhao | |
| 2020/0008655 A1 | 1/2020 | Schlesinger et al. | |
| 2020/0030044 A1 | 1/2020 | Wang et al. | |
| 2020/0030461 A1 | 1/2020 | Sorger | |
| 2020/0038750 A1 | 2/2020 | Kojima | |
| 2020/0043207 A1 | 2/2020 | Lo et al. | |
| 2020/0046431 A1 | 2/2020 | Soper et al. | |
| 2020/0046436 A1 | 2/2020 | Tzeisler et al. | |
| 2020/0054399 A1 | 2/2020 | Duindam et al. | |
| 2020/0060771 A1 | 2/2020 | Lo et al. | |
| 2020/0069192 A1 | 3/2020 | Sanborn et al. | |
| 2020/0077870 A1 | 3/2020 | Dicarlo et al. | |
| 2020/0078095 A1 | 3/2020 | Chopra et al. | |
| 2020/0078103 A1 | 3/2020 | Duindam et al. | |
| 2020/0085514 A1 | 3/2020 | Blumenkranz | |
| 2020/0109124 A1 | 4/2020 | Pomper et al. | |
| 2020/0129045 A1 | 4/2020 | Prisco | |
| 2020/0129239 A1 | 4/2020 | Bianchi et al. | |
| 2020/0138515 A1 | 5/2020 | Wong | |
| 2020/0155116 A1 | 5/2020 | Donhowe et al. | |
| 2020/0170623 A1 | 6/2020 | Averbuch | |
| 2020/0170720 A1 | 6/2020 | Ummalaneni | |
| 2020/0179058 A1 | 6/2020 | Barbagli et al. | |
| 2020/0188038 A1 | 6/2020 | Donhowe et al. | |
| 2020/0205903 A1 | 7/2020 | Srinivasan et al. | |
| 2020/0205904 A1 | 7/2020 | Chopra | |
| 2020/0214664 A1 | 7/2020 | Zhao et al. | |
| 2020/0229679 A1 | 7/2020 | Zhao et al. | |
| 2020/0242767 A1 | 7/2020 | Zhao et al. | |
| 2020/0275869 A1 | 9/2020 | Duindam | |
| 2020/0297442 A1 | 9/2020 | Adebar et al. | |
| 2020/0315554 A1 | 10/2020 | Averbuch et al. | |
| 2020/0330795 A1 | 10/2020 | Sawant et al. | |
| 2020/0352427 A1 | 11/2020 | Deyanov | |
| 2020/0364865 A1 | 11/2020 | Donhowe et al. | |

FOREIGN PATENT DOCUMENTS

| | | |
|---|---|---|
| CZ | 2884879 | 1/2020 |
| EP | 3413830 A4 | 9/2019 |
| EP | 3478161 A4 | 2/2020 |
| EP | 3641686 A2 | 4/2020 |
| EP | 3644885 A1 | 5/2020 |
| EP | 3644886 A1 | 5/2020 |
| MX | PA03005028 A | 1/2004 |
| MX | 225663 B | 1/2005 |
| MX | 226292 | 2/2005 |
| MX | 246862 B | 6/2007 |
| MX | 265247 | 3/2009 |
| MX | 284569 B | 3/2011 |

* cited by examiner

MAGNETIC INTERFERENCE DETECTION SYSTEMS AND METHODS

FIELD

This disclosure relates generally to electromagnetic navigation systems and methods. More particularly, this disclosure is directed to systems and methods for detecting ambient or extraneous magnetic interference in electromagnetic navigation systems and methods.

BACKGROUND

Electromagnetic (EM) navigation systems include multiple coils, which are energized and controlled to generate a low-level magnetic field to determine the location of sensors, e.g., sensors affixed to the distal end portion of a instruments, within the field, e.g., the sensing volume of the magnetic field or EM volume. Additional electronic systems within the proximity of the electromagnetic navigation system, including other electromagnetic navigation systems, may interfere with the low-level magnetic fields. The interference may result in sensor position and orientation measurement inaccuracies. For example, the electromagnetic navigation system may show that a sensor is moving, when, in fact, the sensor is stationary. As a result, the performance of the electromagnetic navigation system may degrade.

SUMMARY

This disclosure relates to electromagnetic navigation systems and methods for detecting ambient or extraneous magnetic interference and alerting the user of the potential degradation of system performance.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a method including: inhibiting a navigation system from generating an electromagnetic field. The method also includes measuring, by a sensor (e.g., a navigation system sensor or navigation system sensors), strength of a magnetic field at a frequency or frequencies of the electromagnetic field generated by the navigation system. The method also includes determining that the strength of the magnetic field is greater than a threshold. The method also includes in response to determining that the strength of the magnetic field is greater than the threshold, displaying, on a display of the navigation system, a message that the magnetic field (e.g., the ambient or background magnetic field) may affect performance of the navigation system. Other embodiments of this aspect include corresponding computer systems, apparatus, and computer programs recorded on one or more computer storage devices, each configured to perform the actions of the methods.

Implementations may include one or more of the following features. The magnetic field may include a time-varying magnetic field. The method may further include measuring the strength of magnetic fields that are in phase with or out of phase from the electromagnetic fields generated by the navigation system. The sensor may include a navigation system sensor, a test sensor, or an antenna array dynamically reconfigured to act as a large area sensor. The navigation system sensor may include a patient sensor or a patient sensor triplet. The navigation system may include radiator coils or test radiator coils. In aspects, inhibiting the navigation system from generating the electromagnetic field may include sending a signal that deactivates the radiator coils. In aspects, the radiator coils may be an antenna array and the method may further include reconfiguring the radiator coils to function as the sensor. In aspects, measuring the magnetic field at the frequency generated by the navigation system may include measuring the magnetic field at frequencies of respective navigation system radiator coils or respective navigation test radiator coils. The method may further include measuring the strength of the magnetic field at a harmonic frequency of the frequency of the electromagnetic field generated by the navigation system. Implementations of the described techniques may include hardware, a method or process, or computer software on a computer-accessible medium.

Another general aspect includes a system including a controller configured to inhibit a navigation system from generating an electromagnetic field. The system also includes a sensor configured to sense a magnetic field at a frequency of the electromagnetic field generated by the navigation system. The system also includes a computing device configured to: acquire a magnetic field measurement from the sensor; determine that a strength of the magnetic field associated with the magnetic field measurement is greater than a threshold; and, in response to determining that the strength of the magnetic field is greater than the threshold, display, on a display of the navigation system, an alert that the magnetic field may affect performance of the navigation system. Other embodiments of this aspect include corresponding computer systems, apparatus, and computer programs recorded on one or more computer storage devices, each configured to perform the actions of the methods.

Implementations may include one or more of the following features. The magnetic field may include a time-varying magnetic field. The sensor may measure a magnetic field at one or more frequencies and phases of the electromagnetic field generated by the navigation system. The sensor may include a navigation system sensor, a test sensor, or an antenna array dynamically reconfigured to act as a large area sensor. In aspects, the navigation system sensor may include a patient sensor or a patient sensor triplet. The sensor may include a sensor disposed on a locatable guide of the navigation system. The sensor may include a sensor disposed on an extended working channel of the navigation system. The navigation system may include a radiator coils. In aspects, measuring the magnetic field at the frequency generated by the navigation system may include measuring the magnetic field at frequencies of respective radiator coils. The computing device may further be configured to measure the strength of the magnetic field at a harmonic frequency of the frequency of the electromagnetic field generated by the navigation system. Implementations of the described techniques may include hardware, a method or process, or computer software on a computer-accessible medium.

Another general aspect includes a navigation system including radiator coils and driver circuitry coupled to the radiator coils and configured to generate electromagnetic energy at different frequencies. The navigation system also includes one or more sensor coils configured to sense a magnetic field and a computing device configured to: send a signal to deactivate the driver circuitry; acquire a magnetic field measurement from the one or more sensor coils;

determine whether the strength of the magnetic field associated with the magnetic field measurement is greater than a threshold to form a determination; and, in response to the determination, generate a message. The navigation system also includes a display configured to display the message. Other embodiments of this aspect include corresponding computer systems, apparatus, and computer programs recorded on one or more computer storage devices, each configured to perform the actions of the methods.

Implementations may include one or more of the following features. In aspects, the determination may be that the strength of the magnetic field is greater than the threshold, and the message may indicate that the magnetic field will affect performance of the navigation system. The determination may also be that the strength of the magnetic field is not greater than the threshold, and the message may indicate that the magnetic field will not affect performance of the navigation system. The computing device may be configured to determine the strength of magnetic fields at different frequencies of the electromagnetic energy and that are in phase with or out of phase from the electromagnetic energy. Implementations of the described techniques may include hardware, a method or process, or computer software on a computer-accessible medium.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

This disclosure relates to electromagnetic navigation systems and methods for detecting ambient or extraneous magnetic interference and alerting the user of potential degradation of system performance. In operation, the electromagnetic navigation systems generate time-varying magnetic fields at various predetermined frequencies. Thus, the electromagnetic navigation systems and methods of this disclosure inhibit the generation of the time-varying magnetic fields and passively listen for and/or actively search for ambient or extraneous magnetic interference which is at the predetermined frequencies and which is in phase with and/or out of phase from the generated magnetic fields. In this way, it is possible to determine whether ambient conditions may degrade system performance and provide an appropriate message or alert to the user.

Figure 1:
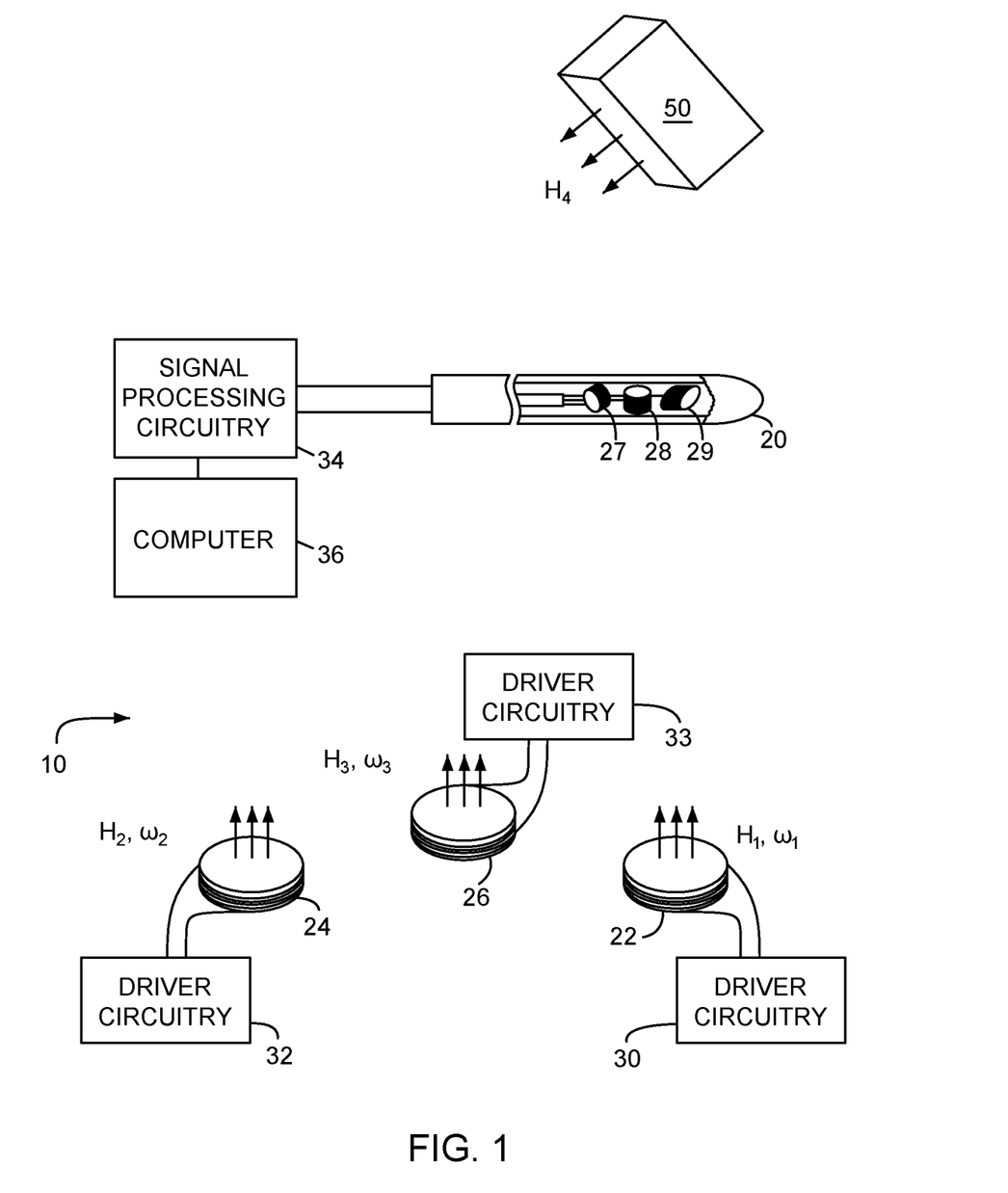
FIG. 1 is a schematic diagram of a navigation system in accordance with an embodiment of the disclosure.

Reference is now made to FIG. 1, which schematically illustrates a system 10 for navigating a probe 20, e.g., a catheter for medical use, according to an example embodiment of this disclosure. System 10 includes radiator coils 22, 24, and 26, although this disclosure contemplates any number of radiator coils, e.g., six or nine radiator coils. In some embodiments, the system 10 may additionally include one or more test radiator coils (not shown), which, for example, may be used while setting up an operation room. Radiator coils 22, 24, and 26 generate respective magnetic fields $H_1$, $H_2$, and $H_3$, which may be time-varying, at respective frequencies $\omega_1$, $\omega_2$, and $\omega_3$, in the vicinity of probe 20. Each frequency $\omega_1$, $\omega_2$, and $\omega_3$ may be divisible by a common frequency $\omega_0$, e.g., $\omega_1 = k_1 \omega_0$, where $k_1$ is a whole number. The values of frequencies $\omega_1$, $\omega_2$, and $\omega_3$ may include frequencies in the range 100 Hz-20 kHz.

System 10 further includes variable frequency driver circuits 30, 32, and 33, which are coupled to respective radiator coils 22, 24, and 26, and which drive respective radiator coils 22, 24, and 26 at the respective frequencies $\omega_1$, $\omega_2$, and $\omega_3$. The frequencies $\omega_1$, $\omega_2$, and $\omega_3$ at which the radiator coils 22, 24, and 26 radiate are set by computer 36. In embodiments, each of the frequencies $\omega_1$, $\omega_2$, and $\omega_3$ may include a range of frequencies, which are stored in memory of the computer 36. In some embodiments, the ranges of frequencies may be mutually exclusive. In embodiments, at least some of the frequencies of each driver circuit 30, 32, and 33, are multiplexed together, and, after acquisition, the resulting signals are analyzed in signal processing circuitry 34. Alternatively, the frequency of each driver circuit is varied according to other methods known in the art, such as scanning the frequencies cyclically over time, and/or using one or more other methods of time multiplexing. Whichever method is used to vary the frequencies, at any instant in time a frequency radiated by a specific coil is set to be different from the frequency or frequencies radiated by all the other coils.

The probe includes sensor coils 27, 28, and 29, although this disclosure contemplates other implementations using more or less than three sensor coils in a sensor. The sensor coils 27, 28, and 29 generate electrical current signals in response to the magnetic fields $H_1$, $H_2$, and $H_3$. At any instant in time the electrical current signals include components of the specific frequencies $\omega_1$, $\omega_2$, and $\omega_3$ being generated, whose respective amplitudes are dependent on the position and orientation of probe 20. The signals generated by sensor coils 27, 28, and 29 are received and processed by signal processing circuitry 34 and then processed by computer 36 to: (a) measure the strength or other characteristics (e.g., direction) of an ambient or extraneous magnetic field when driver circuits 30, 32, and 33 are not energizing the radiator coils 22, 24, and 26, or (b) calculate position and orientation coordinates of the probe 20 when the driver circuits 30, 32, and 33 are energizing the radiator coils 22, 24, and 26.

FIG. 1 shows three radiator coils 22, 24, and 26 and three sensor coils 27, 28, and 29 in a probe 20. Embodiments of this disclosure, however, are applicable to navigation systems including one, two, four, or more radiator coils and one, two, or more sensor coils. For example, this disclosure applies to a single-axis system including one sensor coil and nine radiator coils.

In the absence of parasitic effects, the signals generated by sensor coils 27, 28, and 29 at any of frequencies $\omega_1$ are proportional to the amplitude of the time derivative of the projection of field $H_1$ at probe 20 along the respective axes of the sensor coils. The signals generated at any of frequencies $\omega_2$ and $\omega_3$ are similarly proportional to the projections of $H_2$ and $H_3$.

Since the direction and amplitude of the magnetic field due to any one of radiator coils 22, 24, and 26 can be calculated easily using methods known in the art, the sensor coil signals due to the respective radiator coil field may be directly related to the sensor coil's distance from and orientation relative to the radiator coil. It will also be appreciated that in the absence of parasitic magnetic fields, the phase of the signal at each specific frequency comprised in $\omega_1$, $\omega_2$ and $\omega_3$ is substantially constant relative to the phase of the magnetic field generated by radiator coils 22, 24, and 26, and depends on the position and orientation of sensor coils 27, 28, and 29.

As shown in FIG. 1, however, there may be equipment, which is represented by object 50 and which may or may not be associated with the electromagnetic navigation system, near the probe 20 and the radiator coils 22, 24, and 26, which generates or otherwise emits an ambient or extraneous magnetic field $H_4$ or passively or actively redirects the magnetic field of the system 10, which may negatively impact the performance of the system 10. For example, the ambient or extraneous magnetic field $H_4$ may cause the system 10 to inaccurately determine the position and/or orientation of the probe 20. In the presence of the ambient or extraneous magnetic field $H_4$, the computer may determine that the probe 20 is moving even though it may be stationary. The ambient or extraneous magnetic field $H_4$ originating from the object 50 may be a low-level magnetic field (e.g., a magnetic field in the milli-Tesla range). The ambient or extraneous magnetic field $H_4$ may also be constant or intermittent over time. The object 50 may be medical equipment or other electronic equipment and may be located in the same or a different room from where the system 10 is located.

Figure 2:
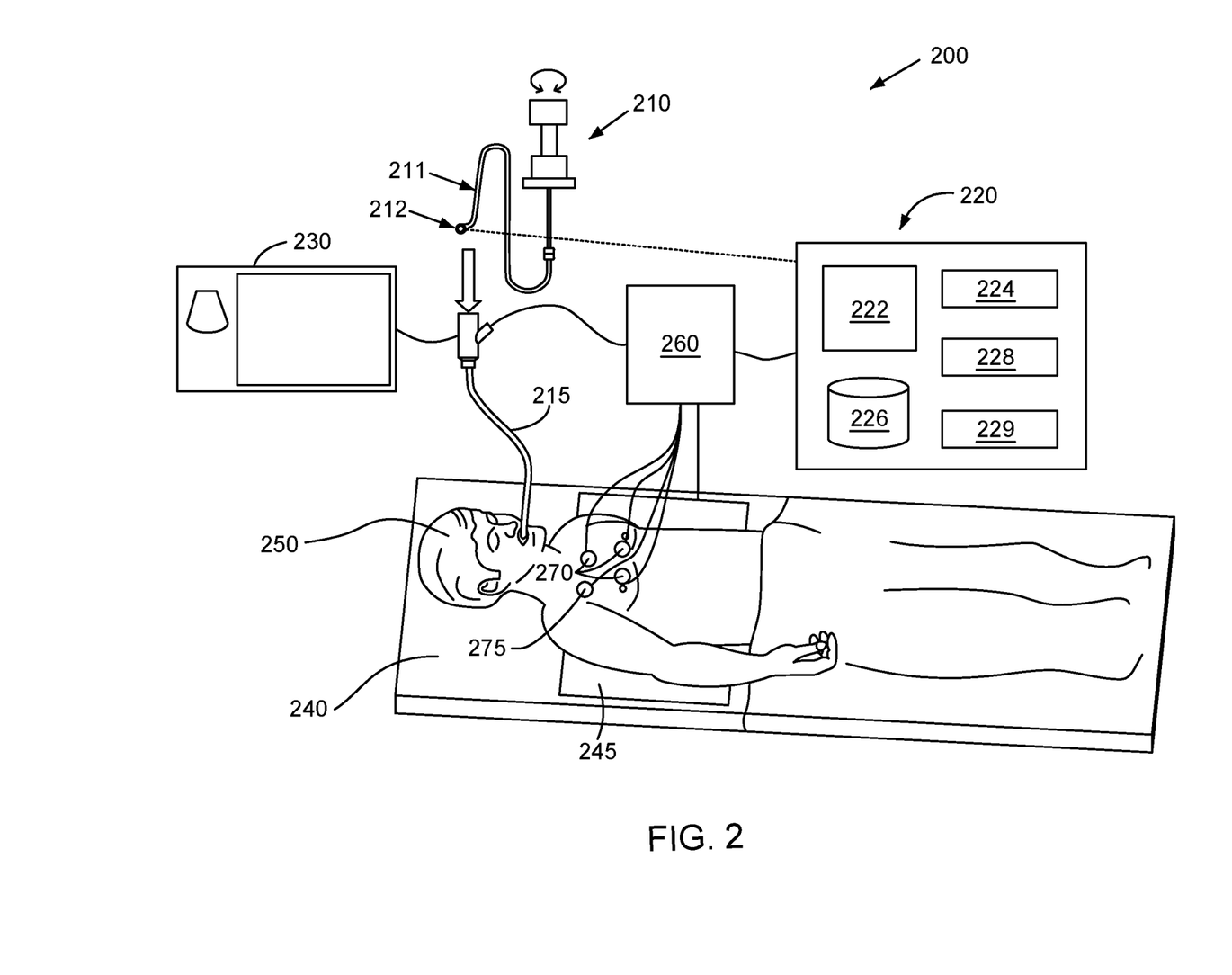
FIG. 2 shows an example electromagnetic navigation (EMN) system in accordance with another embodiment of the disclosure.

FIG. 2 illustrates an example electromagnetic navigation (EMN) system 200, which may employ the ambient or extraneous magnetic field detection systems and methods of this disclosure. The EMN system 200 is configured to identify a location and/or an orientation of a medical device, or sensor thereof, navigating (e.g., to a target) within the patient's body by using an antenna assembly, which includes a plurality of antennas and generates EM fields. The EMN system 200 is further configured to augment CT, MRI, or fluoroscopic images in navigation through patient's body toward a target of interest, such as a diseased portion in a luminal network of a patient's lung.

The EMN system 200 includes a catheter guide assembly 210, a bronchoscope 215, a computing device 220, a monitoring device 230, a bed 240, an antenna assembly 245 that generates an EM field, a tracking device 260, reference sensors 270, and an optional test sensor 275 (or multiple test sensors). The catheter guide assembly 210 is operatively coupled to the computing device 220 and the monitoring device 230 via a wired connection (as shown in FIG. 2) or wireless connection (not shown).

The bronchoscope 215 is inserted into the mouth of a patient 250 and captures images of the luminal network of the lung. In the EMN system 200, inserted into the bronchoscope 215 is a catheter guide assembly 210 for achieving access to the periphery of the luminal network of the lung of the patient 250. The catheter guide assembly 210 may include an extended working channel (EWC) 211 with an EM sensor 212 at the distal portion of the EWC 211. A locatable guide catheter (LG) may be inserted into the EWC 211 with another EM sensor at the distal portion of the LG. In some embodiments, multiple EM sensors (e.g., EM sensor 212) may be disposed on the EWC 211 and/or the LG and the EM sensors may be arranged in an antenna array. The antenna array may be configured to function as a large area magnetic sensor to sense the strength of an ambient or extraneous magnetic field.

The EM sensor 212 at the distal portion of the EWC 211 or the LG is used to identify a location and/or an orientation of the EWC 211 or the LG while navigating through the luminal network of the lung. The EM sensor 212 or antenna array at the distal portion of the EWC 211 or the LG may also be used to measure the strength of an ambient or extraneous magnetic field after the EM field generated by the antenna assembly 245 is turned off or inhibited according to some embodiments of this disclosure. Due to the size restriction in the EWC 211 or the LG, in some embodiments, the EM sensor 212 may include only one single coil for detecting EM field strength of an EM field over the patient 250. However, the number of coils in the EM sensor 212 is not limited to one but may be two or more. Reference or patient sensors 270 placed on the exterior of the patient and referred to collectively as the patient sensor triplet (PST) may be constructed in a manner similar to the EM sensor 212 and may additionally or alternatively provide sensor data to computing device 220 for ambient or extraneous interference detection.

Test sensor 275, which may be placed, for example, on the exterior of the patient, on the bed 240, or anywhere within the EM volume, may also be constructed in a manner similar to the EM sensor 212, in a manner similar to a calibration antenna, in a manner using the antenna assembly 245, or in any other suitable manner known to those skilled in the art. Test sensor 275 may additionally or alternatively provide sensor data to computing device 220 for ambient or extraneous interference detection. In embodiments, the reference sensors 270 or the test sensor 275 may include an active sensor and/or a passive sensor. The active sensor may actively look or search for a magnetic interference signal before an electromagnetic navigation procedure begins. The passive sensor may passively look or search for a magnetic interference signal after the electromagnetic navigation procedure begins. The active and/or passive sensors may be used by the EMN system 200 to passively listen for and/or actively search for ambient or extraneous magnetic interference which is at the resonant and/or center frequencies of the magnetic fields generated by the EMN system 200 and which is in phase with and/or out of phase from the generated magnetic fields.

The computing device 220, such as, a laptop, desktop, tablet, or other similar computing device, includes a display 222, one or more processors 224, memory 226, a network card 228, and an input device 229. The computing device 220 is coupled to the tracking device, which may include an AC current driver (not shown) for providing AC current signals to the antenna assembly 245. The particular configuration of the computing device 220 and the tracking device 260 illustrated in FIG. 2 is provided as an example, but other configurations of the components shown in FIG. 2 as being included in the computing device 220 or tracking device 260 are also contemplated. In particular, in some embodiments, one or more of the components (222, 224, 226, 228, and/or 229) shown in FIG. 2 as being included in the computing device 220 may instead be separate from the computing device 220 and may be coupled to the computing device 220 and/or to any other component(s) of the EMN system 200 by way of one or more respective wired or wireless path(s) to facilitate the transmission of power and/or data signals throughout the EMN system 200. For example, although not shown in FIG. 2, the AC current driver may, in some example aspects, be separate from the tracking device 260 and may be coupled to the antenna assembly 245. In aspects, the computing device 220 may disable the AC current driver prior to detecting or searching for an ambient or extraneous magnetic field and measuring the strength of an ambient or extraneous magnetic field according to embodiments of this disclosure.

In some aspects, the EMN system 200 may also include multiple computing devices, wherein the multiple computing devices are employed for planning, treatment, visualization, helping clinicians in a manner suitable for medical operations, or detecting and measuring the strength of ambient or extraneous magnetic fields. The display 222 may be touch-sensitive and/or voice-activated, enabling the display 222 to serve as both input and output devices. The display 222 may display two-dimensional (2D) images or three-dimensional (3D) models of an anatomic feature. For example, the display 222 may display two-dimensional (2D) images or three-dimensional (3D) models of a lung to locate and identify a portion of the lung that displays symptoms of lung diseases. The display 222 may also display a message (e.g., an alert or pop-up window) indicating whether a detected ambient or extraneous magnetic field will affect performance of the EMN system 200.

The one or more processors 224 execute computer-executable instructions. The processors 224 may perform image-processing functions so that the 3D model of the lung can be displayed on the display 222 or location algorithm to identify a location and an orientation of the EM sensor 212. In embodiments, the computing device 220 may further include a separate graphic accelerator (not shown) that performs the image-processing functions or other processing functions so that the one or more processors 224, e.g., a graphics accelerator, may be available for other programs. The memory 226 stores data and programs. For example, the data may be mapping data for the EMN or any other related data such as a HD map, image data, patients' medical records, prescriptions and/or history of the patient's diseases. The data may also include historical detection and measurement data from detecting and measuring the strength of ambient or extraneous magnetic fields.

The HD map may include a plurality of grid points in a fine coordinate system of the EM volume in which a medical device (e.g., the EWC 211, LG, treatment probe, or other surgical devices) is to be navigated, and expected EM field strengths at each of the plurality of grid points. As the EM sensor 212 senses an EM field strength at a given point, the one or more processors 224, e.g., a graphics processor, compares the sensed EM field strength with the expected EM field strengths in the HD map and identifies the location of the EM sensor 212 within the EM volume. Further, an orientation of the medical device may be also calculated based on the sensed EM field strength and the expected EM field strengths in the HD map.

As shown in FIG. 2, the bed 240 is configured to provide a flat surface for the patient 250 to lie on and a surface to place an antenna assembly 245. When the patient 250 lies on the bed 240 and the antenna assembly 245, the antenna assembly 245 generates an EM field sufficient to project through a portion of the patient 250 or the EM volume. The antenna assembly 245 includes multiple antennas, each of which may include multiple loops. Each antenna is configured to generate an EM waveform having a corresponding frequency. The number of antennas may be at least six and in at least one embodiment is nine so that nine different EM waveforms are generated.

A time multiplexing method may be employed in generating the EM waveforms. For example, the antennas of the antenna assembly 245 may generate EM waveforms with the same frequency at different times during a period. Alternatively, frequency multiplexing method may be employed, where each antenna generates EM waveform having a frequency different from each other. In still another configuration, a combination of the time multiplexing methods and frequency multiplexing methods may be employed. The antennas are grouped into more than one group. Antennas in the same group generate EM waveforms having the same frequency but at different times. Antennas in different groups may generate EM waveforms having different frequencies from each other. A corresponding de-multiplexing method may be used to separate EM waveforms.

Figure 3:
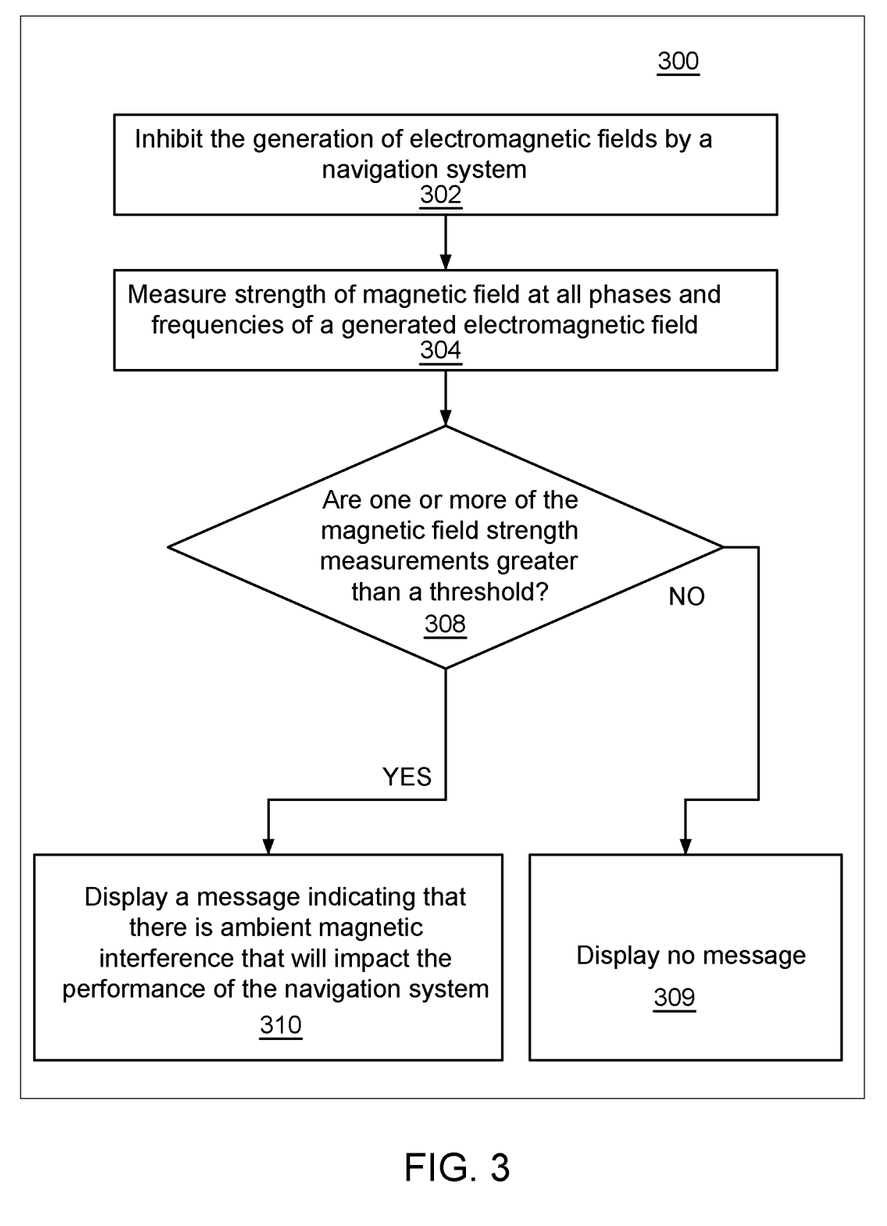
FIG. 3 is a flowchart illustrating a method for detecting magnetic interference in accordance with an embodiment of the disclosure.

FIG. 3 is a flowchart illustrating a method 300 for detecting ambient or extraneous magnetic interference in accordance with embodiments of the disclosure. The method 300 may be implemented by an application running on the computer 36 of FIG. 1. At block 302 of the method 300, the electromagnetic fields generated by the navigation system are inhibited. For example, the application running on the computer 36 may communicate one or more commands to the driver circuits 30, 32, and 33 to cause the driver circuits 30, 32, and 33 to stop driving the radiator coils 22, 24, and 26 with a drive signal. Alternatively, the application running on the computer 36 may turn off the printed circuit board on which the driver circuits 30, 32, and 33 and radiator coils 22, 24, and 26 are disposed.

At block 304, magnetic field strength is measured at all or a portion of the phases and/or frequencies of an electromagnetic (EM) field generated by the navigation system. In embodiments, the magnetic field strength is measured at multiple frequencies of EM fields generated by navigation system radiator coils or navigation test radiator coils. In further embodiments, the magnetic field strength is measured at one or more phases associated with the EM fields generated by navigation system radiator coils or navigation test radiator coils, e.g., in-phase and/or out-of-phase components. In some embodiments, the radiator coils or antennae of the antenna assembly 245 are arranged and/or configured as an antenna array and the radiator coils are dynamically reconfigured to function as a sensor (e.g., a large area magnetic sensor) for measuring the magnetic field strength while the electromagnetic fields generated by the navigation system are inhibited.

As illustrated in FIG. 1, the application running on the computer 36 may communicate one or more commands to the signal processing circuitry 34 to cause the signal processing circuitry 34 to process sensor signals received from the sensor coils 27, 28, and 29. Alternatively or additionally, the application running on the computer 36 may communicate one or more commands to the signal processing circuitry 34 to cause the signal processing circuitry 34 to process sensor signals received from the radiator coils 22, 24, and 26, or the antennae of the antenna assembly 245, which are dynamically reconfigured to function as sensors when they are not being used to generate EM fields.

The signal processing circuitry 34 may acquire phase and/or frequency information from the sensor signals and analyze the phase and/or frequency information to determine whether there is an ambient or extraneous magnetic field that has the same or similar phase and/or frequency as the electromagnetic fields generated by one of the radiator coils 22, 24, and 26, an antenna of the antenna assembly 245, or one or more test radiator coils. The one or more test radiator coils may be used to test the effect of ambient or extraneous magnetic fields on the navigation system at various frequencies of the EM fields generated by the one or more test radiator coils. In some embodiments, the frequency information may include harmonic frequency information.

The signal processing circuitry 34 may also acquire or compute the strength or magnitude of the ambient or extraneous magnetic field at the same or similar phases and frequencies of the electromagnetic fields generated by the radiator coils 22, 24, and 26, the antennae of the antenna assembly 245, or the test radiator coils. In some embodiments, the signal processing circuitry 34 may acquire or compute the strength or magnitude of the ambient or extraneous magnetic field at harmonics of the frequencies of the electromagnetic fields generated by the radiator coils 22, 24, and 26, the antennae of the antenna assembly 245, or the test radiator coils.

In embodiments of this disclosure, the measurement period may range between 8 ms and 10 ms, during which hundreds of measurements (e.g., 800 measurements) may be taken over hundreds of equal time intervals (e.g., 800 equal time intervals). An analog-to-digital converter, which, for example, may reside in the signal processing circuitry 34 and may be coupled to the sensor coils 27, 28, and 29, may be run at a frequency that is at least twice the frequency associated with one time interval.

At block 308, the measured magnetic field strength measurements are compared to a threshold or various thresholds at various frequencies. In some embodiments, the threshold may be determined based on prior experimental testing of the navigation system that indicates how well the navigation system performs when exposed to different magnetic fields strengths.

If, at block 308, one or more of the magnetic field strength measurements is greater than a threshold or various thresholds at various frequencies, a message (e.g., an alert) that there is ambient or extraneous magnetic interference that will impact the performance of the navigation system is displayed at block 310. If, on the other hand, none of the magnetic field strength measurements are greater than a threshold, no message is displayed at block 309, which indicates that the ambient magnetic fields will not impact the performance of the navigation system. In other embodiments, a message, which indicates that the ambient magnetic fields will not impact or affect the performance of the navigation system, may be displayed at block 309.

Figure 4:
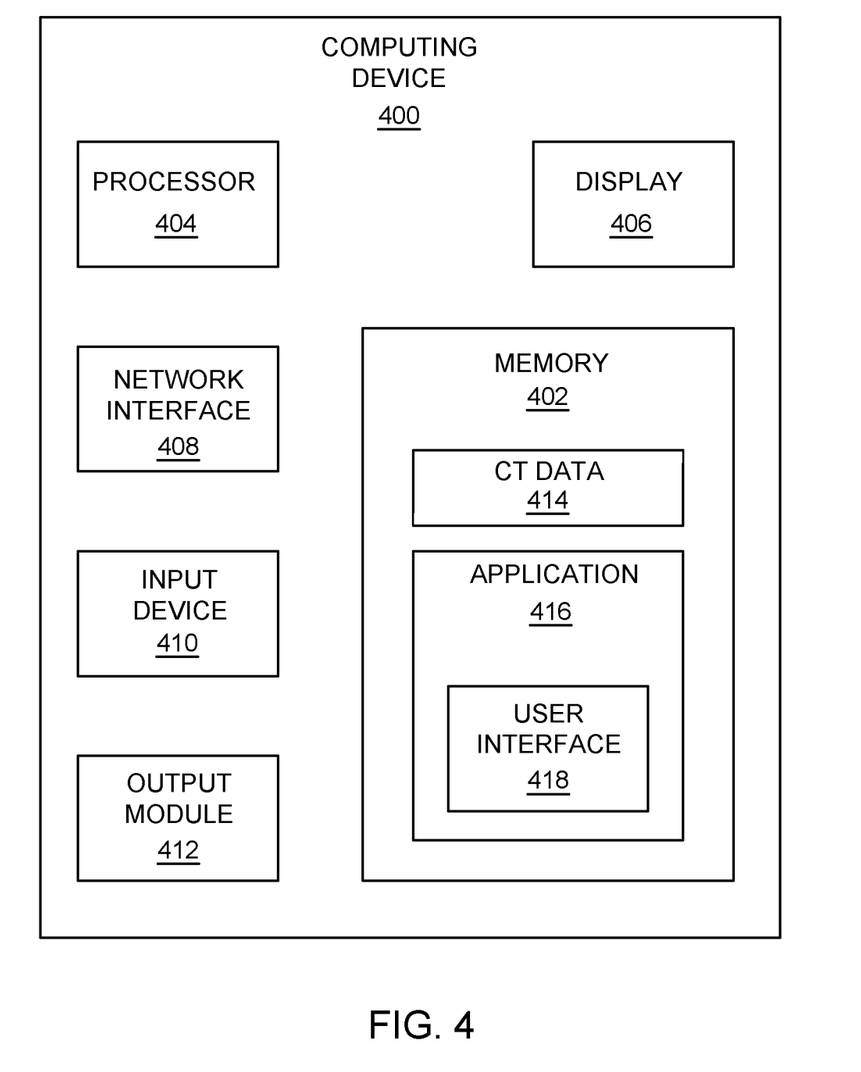
FIG. 4 is a block diagram of the computer or computing device of FIGS. 1 and 2 in accordance with embodiments of the disclosure.

Turning now to FIG. 4, there is shown a block diagram of a computing device 400, which can be used to perform all or a portion of the functions (e.g., the method 300 of FIG. 3) performed by the signal processing circuitry 34 and/or the computer 36 of FIG. 1 or performed by the computing device 220 of FIG. 2. The computing device 400 may include one or more of each of the following components: a memory 402, a processor 404, a display 406, network interface 408, an input device 410, and/or an output module 412.

The memory 402 includes any non-transitory computer-readable storage media for storing data and/or software that is executable by the processor 404 and which controls the operation of the computing device 400. In an embodiment, the memory 402 may include one or more solid-state storage devices such as flash memory chips. Alternatively, or in addition to the one or more solid-state storage devices, the memory 402 may include one or more mass storage devices connected to the processor 404 through a mass storage controller (not shown in FIG. 4) and a communications bus (not shown in FIG. 4). Although the description of computer-readable media contained herein refers to a solid-state storage, it should be appreciated by those skilled in the art that computer-readable storage media can be any available media that can be accessed by the processor 404. That is, computer readable storage media include non-transitory, volatile and non-volatile, removable and non-removable media implemented in any method or technology for storage of information such as computer-readable instructions, data structures, program modules or other data. For example, computer-readable storage media include RAM, ROM, EPROM, EEPROM, flash memory or other solid-state memory technology, CD-ROM, DVD, Blu-Ray or other optical storage, magnetic cassettes, magnetic tape, magnetic disk storage or other magnetic storage devices, or any other medium, which can be used to store the desired information and which can be accessed by the computing device 400.

The memory 402 may store application 416, which may include instructions for performing embodiments of the method 300 of FIG. 3, and/or CT data 414. The application 416 may, when executed by the processor 404, cause the display 406 to present user interface 418 on the display 406.

The processor 404 may be a general purpose processor, a specialized graphic processing unit (GPU) configured to perform specific graphics processing tasks or other processing functions while freeing up the general purpose processor to perform other tasks, a programmable logic device such as a field programmable gate array (FPGA) or complex programmable logic device (CPLD), and/or any number or combination of such processors or devices configured to work independently or cooperatively.

The display 406 may be touch-sensitive and/or voice-activated, enabling the display 406 to serve as both an input and output device. Alternatively, a keyboard (not shown), mouse (not shown), or other data input devices may be employed.

The network interface 408 may be configured to connect to a network, such as a local area network (LAN) including a wired network and/or a wireless network, a wide area network (WAN), a wireless mobile network, a Bluetooth network, and/or the Internet. For example, the computing device 400 may receive settings or parameters (e.g., threshold values for analyzing the measured strength of an ambient or extraneous magnetic field, and/or values of the field strengths and frequencies of the electromagnetic fields generated by the navigation system) to perform the method 300 of FIG. 3. The computing device 400 may receive updates to its software, for example, application 416, via the controller of the network interface 408. The computing device 400 may also display notifications on the display 406 that a software update is available.

In another aspect, the computing device 400 may receive computed tomographic (CT) image data of a patient from a server, for example, a hospital server, Internet server, or other similar servers, for use during surgical or navigational planning. Patient CT image data may also be provided to the computing device 400 via a removable memory (not shown in FIG. 4).

Input device 410 may be any device by means of which a user may interact with the computing device 400, such as, for example, a mouse, keyboard, foot pedal, touch screen, and/or voice interface.

Output module 412 may include any connectivity port or bus, such as, for example, parallel ports, serial ports, universal serial busses (USBs), or any other similar connectivity port known to those skilled in the art.

The application 416 may be one or more software programs stored in the memory 402 and executed by the processor 404 of the computing device 400. In some embodiments, during a planning phase, one or more programs in the application 416 guides a clinician through a series of steps to identify a target, size the target, size a treatment zone, and/or determine an access route to the target for later use during the navigation or procedure phase. In other embodiments, one or more software programs in the application 416 may be loaded on computing devices in an operating room or other facility where surgical procedures are performed, and the application 416 is used as a plan or map to guide a clinician performing a surgical procedure. Prior to performing the surgical procedure, one or more software programs in the application 416 may be loaded from the memory 402 and executed by the processor 404 to disable the AC current driver that provides AC current signals to energize the antenna assembly 245 and to detect and/or measure the strength of ambient or extraneous magnetic fields.

The application 416 may be installed directly on the computing device 400, or may be installed on another computer, for example a central server, and opened on the computing device 400 via the network interface 408. Application 416 may run natively on the computing device 400, as a web-based application, or any other format known to those skilled in the art. In some embodiments, the application 416 will be a single software program having all of the features and functionality described in this disclosure. In other embodiments, the application 416 may be two or more distinct software programs providing various parts of these features and functionality. For example, the application 416 may include one software program for processing sensor data to determine the strength of an ambient magnetic field, another one for determining whether the determined strength is greater than a threshold, and a third program for generating an appropriate message and transmitting the message to the display 406. In such instances, the various software programs forming part of the application 416 may be enabled to communicate with each other and/or import and export various data including settings and parameters relating to the detection of and measurement of the strength of ambient or extraneous magnetic fields.

The application 416 may communicate with a user interface 418 which generates a user interface for presenting visual interactive features to a user, for example, on the display 46 and for receiving input, for example, via a user input device (410). For example, user interface 418 may generate a graphical user interface (GUI) and output the GUI to the display 46 for viewing by a user. The GUI may include a window that displays information regarding ambient or extraneous magnetic fields that may affect the performance of the EMN system 200. The information may include an estimated distance from the EMN system 200 to the magnetic field source or other information that would help the operator of the EMN system 200 to locate the magnetic field source and minimize its effects on the operation of the EMN system 200.

In a case where the computing device 400 is configured to implement the EMN system 200, the computing device 220, or the tracking device 260, the computing device 400 may be linked to the monitoring device 230, thus enabling the computing device 400 to control the output on the monitoring device 230 along with the output on the display 406. The computing device 400 may control the monitoring device 230 to display output which is the same as or similar to the output displayed on the display 406. For example, the output on the display 406 may be mirrored on the monitoring device 230. Alternatively, the computing device 400 may control the monitoring device 230 to display different output from that displayed on the display 406. For example, the monitoring device 230 may be controlled to display guidance images and information during the surgical or navigation procedure, while the display 406 is controlled to display other output, such as configuration or status information of an electro surgical generator (not shown in FIG. 2).

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed is:

1. A method comprising:
   inhibiting a navigation system from generating an electromagnetic field;
   measuring, by a sensor of the navigation system, strength of a magnetic field at a frequency of the electromagnetic field generated by the navigation system in response to inhibiting the navigation system;
   determining that the strength of the magnetic field is greater than a threshold; and
   in response to determining that the strength of the magnetic field is greater than the threshold, displaying, on a display of the navigation system, a message that the magnetic field may affect performance of the navigation system.

2. The method of claim 1, wherein the magnetic field is a time-varying magnetic field.

3. The method of claim 1, further comprising measuring strength of magnetic fields that are in phase with or out of phase from the electromagnetic field generated by the navigation system.

4. The method of claim 1, wherein the sensor is a navigation system sensor, a test sensor, or an antenna array dynamically reconfigured to act as a large area sensor.

5. The method of claim 4, wherein the navigation system sensor is a patient sensor or a patient sensor triplet.

6. The method of claim 1, wherein the navigation system includes a plurality of radiator coils or a plurality of test radiator coils.

7. The method of claim 6, wherein inhibiting the navigation system from generating the electromagnetic field includes sending a signal that deactivates the plurality of radiator coils.

8. The method of claim 7, wherein the plurality of radiator coils is an antenna array and the method further comprises reconfiguring the plurality of radiator coils to function as the sensor.

9. The method of claim 1, wherein measuring the magnetic field at the frequency generated by the navigation system includes measuring the magnetic field at a plurality of frequencies of a respective plurality of navigation system radiator coils or a respective plurality of navigation test radiator coils.

10. The method of claim 1, further comprising measuring the strength of the magnetic field at a harmonic frequency of the frequency of the electromagnetic field generated by the navigation system.

11. A system comprising:
a controller configured to inhibit a navigation system from generating an electromagnetic field;
a sensor of the navigation system configured to sense a magnetic field at a frequency of the electromagnetic field generated by the navigation system; and
a computing device configured to:
acquire a magnetic field measurement from the sensor in response to inhibiting the navigation system;
determine that a strength of the magnetic field associated with the magnetic field measurement is greater than a threshold; and
in response to determining that the strength of the magnetic field is greater than the threshold, display, on a display of the navigation system, an alert that the magnetic field may affect performance of the navigation system.

12. The system of claim 11, wherein the magnetic field is a time-varying magnetic field.

13. The system of claim 11, wherein the sensor measures a magnetic field at one or more phases of the electromagnetic field generated by the navigation system.

14. The system of claim 11, wherein the sensor is a navigation system sensor, a test sensor, or an antenna array dynamically reconfigured to act as a large area sensor.

15. The system of claim 14, wherein the navigation system sensor is a patient sensor or a patient sensor triplet.

16. The system of claim 11, wherein the sensor is a sensor disposed on a locatable guide or on an extended working channel of the navigation system.

17. The system of claim 11, wherein the navigation system includes a plurality of radiator coils or a plurality of test radiator coils.

18. The system of claim 11, wherein measuring the magnetic field at the frequency generated by the navigation system includes measuring the magnetic field at a plurality of frequencies of a respective plurality of radiator coils or a respective plurality of test radiator coils.

19. A navigation system comprising:
a plurality of radiator coils;
driver circuitry coupled to the plurality of radiator coils and configured to generate electromagnetic energy at a plurality of different frequencies;
one or more sensor coils configured to sense a magnetic field;
a computing device configured to:
determine a position of the one or more sensor coils based on the magnetic field sensed by the one or more sensor coils;
send a signal to deactivate the driver circuitry;
acquire a magnetic field measurement from the one or more sensor coils in response to sending the signal to deactivate the driver circuitry;
determine whether a strength of the magnetic field associated with the magnetic field measurement is greater than a threshold, yielding a determination; and
in response to the determination, generate a message; and
a display configured to display the message.

20. The navigation system of claim 19, wherein the determination is that the strength of the magnetic field is greater than the threshold, and the message indicates that the magnetic field will affect performance of the navigation system.

* * * * *